(12) United States Patent
Harris

(10) Patent No.: US 9,227,181 B2
(45) Date of Patent: Jan. 5, 2016

(54) CATALYST TO INCREASE PROPYLENE YIELDS FROM A FLUID CATALYTIC CRACKING UNIT

(75) Inventor: David H. Harris, Mountainside, NJ (US)

(73) Assignee: BASF Corporation, Florham Park, NJ (US)

( * ) Notice: Subject to any disclaimer, the term of this patent is extended or adjusted under 35 U.S.C. 154(b) by 1099 days.

(21) Appl. No.: 13/231,522

(22) Filed: Sep. 13, 2011

(65) Prior Publication Data

US 2013/0066131 A1 Mar. 14, 2013

(51) Int. Cl.

| | |
|---|---|
| B01J 29/06 | (2006.01) |
| C10G 11/18 | (2006.01) |
| B01J 29/80 | (2006.01) |
| B01J 29/40 | (2006.01) |
| B01J 37/28 | (2006.01) |
| C07C 4/06 | (2006.01) |
| B01J 29/08 | (2006.01) |
| B01J 29/70 | (2006.01) |
| B01J 35/10 | (2006.01) |

(52) U.S. Cl.
CPC *B01J 29/80* (2013.01); *B01J 29/40* (2013.01); *B01J 37/28* (2013.01); *C07C 4/06* (2013.01); *C10G 11/18* (2013.01); *B01J 29/084* (2013.01); *B01J 29/088* (2013.01); *B01J 29/7007* (2013.01); *B01J 35/1066* (2013.01); *B01J 2229/42* (2013.01); *C07C 2529/08* (2013.01); *C07C 2529/40* (2013.01); *C07C 2529/70* (2013.01); *C07C 2529/80* (2013.01)

(58) Field of Classification Search
USPC .............. 502/63, 64, 65, 67, 69, 71; 585/653; 208/119, 120.01, 120.05, 121, 122
See application file for complete search history.

(56) References Cited

U.S. PATENT DOCUMENTS

| | | | |
|---|---|---|---|
| 3,758,403 | A | 9/1973 | Rosinski et al. |
| 5,183,790 | A | 2/1993 | Chitnis et al. |
| 5,279,726 | A | 1/1994 | Ward |
| 5,536,687 | A | 7/1996 | Ward |
| 5,888,378 | A | 3/1999 | Kowalski |
| 6,538,169 | B1 | 3/2003 | Pittman et al. |
| 6,656,347 | B2 | 12/2003 | Stockwell et al. |
| 7,326,332 | B2 | 2/2008 | Chen et al. |
| 7,375,048 | B2 | 5/2008 | Smith et al. |
| 2007/0209969 | A1 | 9/2007 | Shen et al. |
| 2009/0101543 | A1 | 4/2009 | Shen et al. |
| 2009/0124842 | A1 | 5/2009 | Reagan et al. |
| 2009/0325786 | A1 | 12/2009 | Liu et al. |

FOREIGN PATENT DOCUMENTS

| | | |
|---|---|---|
| CN | 1354224 | 6/2002 |
| CN | 101190864 | 6/2008 |
| CN | 101279284 | 10/2008 |
| CN | 101279880 | 10/2008 |
| DE | 4114532 | 11/1991 |
| EP | 0278830 | 8/1988 |
| EP | 0489723 | 6/1992 |
| EP | 2075068 | 7/2009 |
| WO | 9502635 | 1/1995 |
| WO | WO9502653 | 1/1995 |
| WO | 2008028949 | 3/2008 |
| WO | 2008034299 | 3/2008 |

OTHER PUBLICATIONS

International Preliminary Report on Patentability dated Mar. 17, 2015.

*Primary Examiner* — Elizabeth Wood
(74) *Attorney, Agent, or Firm* — Foley & Lardner LLP

(57) ABSTRACT

A catalyst composition resulting in increased propylene yields during fluid catalytic cracking processes comprises (i) Y zeolite, (ii) ZSM-5 zeolite, and (iii) Beta zeolite.

19 Claims, No Drawings

CATALYST TO INCREASE PROPYLENE YIELDS FROM A FLUID CATALYTIC CRACKING UNIT

FIELD OF THE INVENTION

The present invention provides a novel catalyst composition for increasing propylene yields during fluid catalytic cracking.

BACKGROUND OF THE INVENTION

Catalytic cracking, and particularly fluid catalytic cracking (FCC), is routinely used to convert heavy hydrocarbon feedstocks to lighter products, such as gasoline and distillate range fractions. There is, however, an increasing need to enhance the yield of light olefins, especially propylene, in the product slate from catalytic cracking processes. Light olefins (C2-C4 olefins) are important feedstocks for the petrochemical industry. Propylene, for example, a light olefin hydrocarbon with three carbon atoms per molecule, is an important chemical for use in the production of other useful materials, such as polypropylene. Polypropylene is one of the most common plastics found in use today and has a wide variety of uses for both as a fabrication material and as a material for packaging.

To produce light olefins, the catalytic cracking of heavy hydrocarbon feedstocks, such as naphtha, is typically carried out by contacting a naphtha-containing feed with a catalyst composition usually comprised of one or more crystalline microporous molecular sieves to selectively convert the feed into an olefin-containing mixture. Although various naphtha catalytic cracking processes have been proposed in the past, many of the processes do not produce commercially important light olefins, e.g., propylene, with sufficient selectivity or yield. Also, the cracking processes can produce undesirable amounts of methane and aromatics as unwanted byproducts. In contrast, a practical and economic naphtha catalytic cracking process should selectively produce increased amounts of light olefins, e.g., propylene, while producing minimal amounts of methane and aromatics.

In FCC processes, a hydrocarbon feedstock is injected into the riser section of a FCC reactor, where the feedstock is cracked into lighter, more valuable products upon contacting hot catalyst circulated to the riser-reactor from a catalyst regenerator. A major breakthrough in FCC catalysts came in the early 1960s, with the introduction of molecular sieves or zeolites. These materials were incorporated into the matrix of amorphous and/or amorphous/kaolin materials constituting the FCC catalysts of that time. These new zeolitic catalysts, containing a crystalline aluminosilicate zeolite in an amorphous or amorphous/kaolin matrix of silica, alumina, silica-alumina, kaolin, clay or the like were at least 1,000-10,000 times more active for cracking hydrocarbons than the earlier amorphous or amorphous/kaolin containing silica-alumina catalysts. This introduction of zeolitic cracking catalysts revolutionized the fluid catalytic cracking process. New processes were developed to handle these high activities, such as riser cracking, shortened contact times, new regeneration processes, new improved zeolitic catalyst developments, and the like.

The zeolites typically used in FCC are crystalline aluminosilicates which have a uniform crystal structure characterized by a large number of regular small cavities interconnected by a large number of even smaller channels. It was discovered that, by virtue of this structure consisting of a network of interconnected uniformly sized cavities and channels, crystalline zeolites are able to accept, for absorption, molecules having sizes below a certain well defined value while rejecting molecules of larger sizes, and for this reason they have come to be known as "molecular sieves." This characteristic structure also gives them catalytic properties, especially for certain types of hydrocarbon conversions.

In current commercial practice, most FCC cracking catalysts used throughout the world are made of a catalytically active component large-pore zeolite. Conventional large-pore molecular sieves include zeolite X; REX; zeolite Y; Ultrastable Y (USY); Rare Earth exchanged Y (REY); Rare Earth exchanged USY (REUSY); Dealuminated Y (DeAl Y); Ultrahydrophobic Y (UHPY); and/or dealuminated silicon-enriched zeolites, e.g., LZ-210. ZSM-20, zeolite L and naturally occurring zeolites such as faujasite, mordenite and the like have also been used.

In addition to large pore zeolites, the ZSM family of zeolites is well known and their preparation and properties have been extensively described in the catalytic cracking of hydrocarbons. For example, one type of the ZSM family of zeolites is that known as ZSM-5. The crystalline aluminosilicate zeolite known as ZSM-5 is particularly described in U.S. Pat. No. 3,702,886, the disclosure of which is incorporated herein by reference. ZSM-5 crystalline aluminosilicate is characterized by a silica-to-alumina mole ratio of greater than 5 and more precisely in the anhydrous state by the general formula:

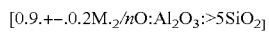

$$[0.9.+-.0.2M_{2/n}O:Al_2O_3:>5SiO_2]$$

wherein M having a valence n is selected from the group consisting of a mixture of alkali metal cations and organo ammonium cations, particularly a mixture of sodium and tetraalkyl ammonium cations, the alkyl groups of which preferably contain 2 to 5 carbon atoms. The term "anhydrous" as used in the above context means that molecular water is not included in the formula. In general, the mole ratio of $SiO_2$ to $Al_2O_3$ for a ZSM-5 zeolite can vary widely. For example, ZSM-5 zeolites can be aluminum-free in which the ZSM-5 is formed from an alkali mixture of silica containing only impurities of aluminum. All zeolites characterized as ZSM-5, however, will have the characteristic X-ray diffraction pattern set forth in U.S. Pat. No. 3,702,886 regardless of the aluminum content of the zeolite.

Beta zeolite is another zeolite that can be used in the catalytic cracking of hydrocarbons. Beta zeolite is typically a silicon-rich large pore zeolite having a three-dimensional pore structure, and has both acid catalytic properties and structural selectivity due to its structural particularity, and further has very high thermostability (the failure temperature of the crystal lattice is higher than 1200° C.), hydrothermal stability and abrasion-resistant properties. Due to the unique structural features, thereof, the zeolite beta has good thermal and hydrothermal stability, acid resistance, anti-coking properties and catalytic activity in a series of catalytic reactions. It has thus developed rapidly for new catalytic processes in recent years.

The catalysts used in FCC processing have been tailored to maximize the performance in specific hydrocarbon conversion processes. For instance, the catalyst compositions used in hydrocarbon conversion processes have been made into multifunctional catalysts, e.g., a bifunctional catalyst or a trifunctional catalyst. A bifunctional catalyst comprises two separate catalysts, e.g., two zeolites having different compositions or structure types, which induce separate reactions. The reaction products can be separate or the two catalysts can be used together such that the reaction product of one catalyst is transported to and reacts on a catalyst site of the second catalyst. Also, since one of the benefits of using a zeolite catalyst is that the catalyst is shape selective and non-selective reactions on the surface of the zeolite are usually not desirable, zeolite catalysts used in hydrocarbon conversion processes have the capability of preventing or at least reducing unwanted reactions which may take place on the surface of the zeolite catalyst by selectively sieving molecules in the feedstream based on their size or shape. Thus, undesirable molecules present in the feedstream are prevented from entering the pores of the catalyst and reacting. In addition, the performance of a zeolite catalyst can sometimes be maximized if the catalyst selectively sieves desired molecules based on their size or shape in order to prevent the molecules from exiting the pores of the catalyst.

Hydrocarbon conversions using catalyst compositions containing two different zeolites have been used in the past. For example, in order to increase the octane number of the gasoline fraction, a catalyst composition containing a large pore molecular sieve, such as zeolite Y, as the primary cracking component and a medium pore zeolite, such as ZSM-5, added to the zeolite Y cracking catalyst is typically used in conventional processes for catalytic cracking of heavy hydrocarbon feedstocks to gasoline and distillate fractions. U.S. Pat. No. 3,758,403 discloses a catalyst using ZSM-5 zeolite and a large pore zeolite such as zeolite Y (with a ratio of 1:10 to 3:1) as active components. In addition to enhancing the octane number of the gasoline, this catalyst mixture provides a higher yield of $C_3$ and $C_4$ olefins.

It is also known, e.g. from U.S. Pat. No. 5,279,726 and EP 559,646, to form composites of two different aluminosilicates, a Y zeolite and zeolite beta, for use in hydrocarbon cracking. In U.S. Pat. No. 5,279,726 a hydrocracking catalyst is disclosed having high activity and selectivity for gasoline which comprises a hydrogenation component on a catalyst support comprising both zeolite beta and a Y zeolite. In addition, U.S. Pat. No. 5,536,687 involves a hydrocracking process using a catalyst containing crystals of zeolite beta and zeolite Y that are bound by an amorphous binder material such as alumina.

In addition, CN 1103105A and EP-2-075-068 A1 describe the use of catalyst compositions comprising three different zeolites in hydrocarbon cracking. CN 1103105A discloses a cracking catalyst capable of giving a higher yield of isobutene and isopentene than without the catalyst and can coproduce high octane level gasoline. The components and contents of the catalyst described in CN 1103105A are as follows: (1) 5-25 wt. % modified HZSM-5 with a silicon:aluminum ratio of 20-100; (2) 1-5 wt. % of high silicon HZSM with a silicon:aluminum ratio of 250-450; (3) 5-20 wt. % of USY zeolite; (4) 1-5 wt. % of beta zeolite; (5) 30-60 wt. % of natural clay; and (6) 15-30 wt. % of inorganic oxide. EP-2-075-068 A1 describes a catalyst composition with a zeolite mixture as follows: (1) 1-75 wt. % of a zeolite beta modified with phosphorus and a transition metal; (2) 25-99 wt. % of a zeolite having a MFI structure, such as ZSM-5; and (3) 0-74 wt. % of a large pore zeolite, such as a Y zeolite.

To increase the yields of light olefins during the hydrocarbon cracking process, a zeolite cracking catalyst with added phosphorus has been used. WO 98/41595 discloses that the addition of a phosphorus-containing, medium pore zeolite, such as ZSM-5, to a conventional large pore molecular sieve cracking catalyst increases the yield of $C_3$ to $C_5$ olefins in the catalytic cracking of hydrocarbon feedstocks without significant loss in the aging characteristics of the medium pore additive. Thus, the yield of $C_4$ and $C_5$ olefins in catalytic cracking can be enhanced by adding a phosphorus-containing medium pore zeolite, such as ZSM-5, to a conventional zeolite Y cracking catalyst.

Incorporation of the phosphorus in the medium pore zeolite is conveniently achieved by the methods described in U.S. Pat. Nos. 4,356,338, 5,110,776, and 5,231,064. Treatment with phosphorus-containing compounds can readily be accomplished by contacting the zeolite, either alone or in combination with a binder or matrix material, with a solution of an appropriate phosphorus compound, followed by drying and calcining to convert the phosphorus to its oxide form.

While the current FCC process of using various combinations of zeolite Y, beta zeolite, and ZSM-5 is an efficient process for converting heavier feed to lighter products, many times the process makes less than desirable amounts of light olefins like propylene. Growth in the polypropylene market is expected to drive the demand for propylene, and a production process of propylene via an FCC process that is more selective towards propylene than the prior art catalyst compositions is desired.

SUMMARY OF THE INVENTION

The objective of this invention is to develop a petrochemical fluid catalytic cracking catalyst blend that results in a significant increase in propylene yield compared to the current state of the art petrochemical FCC catalyst systems. This invention supplements known blends of Y zeolite and ZSM-5, with an additional additive containing Beta zeolite.

DETAILED DESCRIPTION OF THE INVENTION

The objective of this invention is to develop a petrochemical FCC catalyst system that results in a significant increase in propylene yield compared to the current state of the art petrochemical FCC catalyst systems. Current petrochemical catalyst systems typically consist of a blend of a large pore catalyst, such as a Y zeolite based FCC catalyst, and an additive zeolite, such as ZSM-5. This invention proposes supplementing the current catalyst blend with an additional additive containing Beta zeolite.

In order to achieve the desired increase in propylene yield, the present invention provides a catalyst blend, which comprises, based on the total weight of the catalyst blend, 5-50 wt. % zeolite Y, 5-40 wt. % ZSM-5, and 35-70 wt. % Beta catalyst. In another embodiment, the catalyst composition comprises 25-30 wt. % zeolite Y, 15-20 wt. % ZSM-5, 50-60 wt. % Beta catalyst. The weight percent for each zeolite, as expressed immediately above and hereinafter, including the appended claims, pertains to the active zeolite component and any matrix, binder or additive components.

FCC catalysts are often blends of a catalytically active large-pore zeolite component and additives containing other zeolites. Large pore cracking catalysts have pore openings of greater than about 7 Angstroms in effective diameter. Conventional large-pore molecular sieves include zeolite X (U.S. Pat. No. 2,882,442); REX; zeolite Y (U.S. Pat. No. 3,130, 007); Ultrastable Y (USY) (U.S. Pat. No. 3,449,070); Rare Earth exchanged Y (REY) (U.S. Pat. No. 4,415,438); Rare Earth exchanged USY (REUSY); Dealuminated Y (DeAl Y) (U.S. Pat. Nos. 3,442,792 and 4,331,694); Ultrahydrophobic Y (UHPY) (U.S. Pat. No. 4,401,556); and/or dealuminated silicon-enriched zeolites, e.g., LZ-210 (U.S. Pat. No. 4,678, 765). Generally preferred are higher silica forms of zeolite Y. ZSM-20 (U.S. Pat. No. 3,972,983) and zeolite L (U.S. Pat. Nos. 3,216,789 and 4,701,315); and naturally occurring zeolites such as faujasite, mordenite and the like may also be used (with all patents above in parentheses incorporated herein by reference). These materials may be subjected to conventional treatments, such as impregnation or ion exchange with rare earths to increase stability. In current commercial practice most cracking catalysts contain these large-pore molecular sieves.

Other large-pore crystalline molecular sieves include pillared silicates and/or clays; aluminophosphates, e.g., AIPO-4-5, AIPO-4-8, VPI-5; silicoaluminophosphates, e.g., SAPO-5, SAPO-37, SAPO-40, MCM-9; and other metal aluminophosphates. Mesoporous crystalline material for use as the molecular sieve includes MCM-41. These are variously described in U.S. Pat. Nos. 4,310,440; 4,440,871; 4,554,143; 4,567,029; 4,666,875; 4,742,033; 4,880,611; 4,859,314; 4,791,083; 5,102,643; and 5,098,684, each incorporated herein by reference.

The preferred molecular sieve of those listed above is a zeolite Y, more preferably a REY, USY or REUSY. In general, the zeolite Y is incorporated into an amorphous binder as is well known in the art. Suitable binders include silica, silica-alumina, alumina, clay or other known inorganic binders.

In another embodiment of the invention, zeolite Y could be produced into high zeolite content microspheres by the in-situ procedure described in U.S. Pat. No. 4,493,902, the teachings of which are incorporated herein by cross-reference. The '902 patent discloses novel fluid cracking catalysts comprising attrition-resistant, high zeolitic content, catalytically active microspheres containing more than about 40%, preferably 50-70% by weight Y faujasite and methods for making such catalysts by crystallizing more than about 40% sodium Y zeolite in porous microspheres composed of a mixture of metakaolin (kaolin calcined to undergo a strong endothermic reaction associated with dehydroxylation) and kaolin calcined under conditions more severe than those used to convert kaolin to metakaolin, i.e., kaolin calcined to undergo the characteristic kaolin exothermic reaction, sometimes referred to as the spinel form of calcined kaolin. The microspheres containing the two forms of calcined kaolin could also be immersed in an alkaline sodium silicate solution, which is heated, preferably until the maximum obtainable amount of Y faujasite is crystallized in the microspheres.

In carrying out the invention described in the '902 patent, the microspheres composed of kaolin calcined to undergo the exotherm and metakaolin are reacted with a caustic enriched sodium silicate solution in the presence of a crystallization initiator (seeds) to convert silica and alumina in the microspheres into synthetic sodium faujasite (zeolite Y). The microspheres are separated from the sodium silicate mother liquor, ion-exchanged with rare earth, ammonium ions or both to form rare earth or various known stabilized forms of catalysts. The technology of the '902 patent provides means for achieving a desirable and unique combination of high zeolite content associated with high activity, good selectivity and thermal stability, as well as attrition-resistance.

In another embodiment of the invention, zeolite Y could be produced as novel zeolite microspheres, known as the Naphthamax® catalyst from BASF Catalysts, which are disclosed in U.S. Pat. No. 6,656,347. These zeolite microspheres are macroporous, have sufficient levels of zeolite to be very active and are of a unique morphology to achieve effective conversion of hydrocarbons to cracked gasoline products with improved bottoms cracking under short contact time FCC processing. The novel zeolite microspheres are produced by novel processing, which is a modification of technology described in the '902 patent. It has been found that if the non-zeolite, alumina-rich matrix of the catalyst is derived from an ultrafine hydrous kaolin source having a particulate size such that 90 wt. % of the hydrous kaolin particles are less than 2 microns, and which is pulverized and calcined through the exotherm, a macroporous zeolite microsphere can be produced. More generally, the FCC catalyst matrix useful to achieve FCC catalyst macroporosity is derived from alumina sources, such as kaolin calcined through the exotherm, that have a specified water pore volume, which distinguishes over prior art calcined kaolin used to form the catalyst matrix. The water pore volume is derived from an Incipient Slurry Point (ISP) test, which is described in the patent.

The morphology of the microsphere catalysts which are formed is unique relative to the in-situ microsphere catalysts formed previously. Use of a pulverized, ultrafine hydrous kaolin calcined through the exotherm yields in-situ zeolite microspheres having a macroporous structure in which the macropores of the structure are essentially coated or lined with zeolite subsequent to crystallization. Macroporosity as defined herein means the catalyst has a macropore volume in the pore range of 600-20,000 angstroms of at least 0.07 cc/gm mercury intrusion, preferably at least 0.10 cc/gm mercury intrusion. The novel catalyst is optimal for FCC processing, including the short contact time processing in which the hydrocarbon feed is contacted with a catalyst for times of about 3 seconds or less.

In the broadest sense, the Naphthamax® as described in U.S. Pat. No. 6,656,347 is not restricted to macroporous catalysts having a non-zeolite matrix derived solely from kaolin. Thus, any alumina source which has the proper combinations of porosity and reactivity during zeolite synthesis and can generate the desired catalyst macroporosity and morphology can be used. The desired morphology comprises a matrix which is well dispersed throughout the catalyst, and the macropore walls of matrix are lined with zeolite and are substantially free of binder coatings. Accordingly, not only is the large pore surface area of the catalyst vastly improved over previous catalysts, and the active matrix dispersed throughout the microsphere, the zeolite crystals are readily accessible to the hydrocarbon feed. While not wishing to be bound by any theory of operation, it appears that previous catalysts in which the zeolite is incorporated into a matrix by physical mixing and glued with binder have sufficient macroporosity, however the binder coats the active zeolite catalyst thereby blocking accessibility thereto. The Naphthamax® microsphere catalysts have a morphology which allows fast diffusion into the catalyst due to the macroporosity and enhanced dispersion of the matrix, and further provides the highest accessibility to the zeolite inasmuch as the zeolite is freely coated onto the walls of the pores. The term "freely" means that the zeolite phase is present on the surface of the matrix and is unobstructed by any binder phases. Merely having macroporosity does not provide the results that have been obtained, since conventional incorporated catalysts have similar macroporosity. It is therefore the combination of porosity and zeolite-coated macropore walls that give the surprising selectivity results.

In another embodiment of the invention, zeolite Y is a rare earth exchanged Y zeolite crystallized in-situ in a porous kaolin matrix. In another embodiment of the invention, zeolite Y contains up to 12% of a rare earth element ion exchanged onto the Y zeolite.

For the present invention, ZSM-5 is blended with the Y zeolite. Based on the unique pore structure of ZSM-5, this zeolite can be applied extensively as a catalyst material to various processes. Zeolite ZSM-5 has been shown to be a particularly useful catalyst in reactions involving aromatic compounds, with emphasis on those having a single carbocycle. Thus ZSM-5 exhibits unique selectivity in the conversion of olefins, naphthenes, alcohols, ethers and alkanes into aromatic compounds and in such reactions as isomerization, alkylation, dealkylation and transalkylation of aromatics. That favorable influence on aromatic conversion reactions is found also in the forms of ZSM-5 in which another metal appears in isomorphic substitution for aluminum, as described in U.S. Pat. No. 4,163,028. ZSM-5 has also been extensively applied in catalytic cracking and catalytic dewaxing. When ZSM-5 is used in catalytic cracking of petroleum, enhancement of gasoline octane is achieved. Accordingly, ZSM-5 has been used as an additive to other cracking catalysts, e.g. zeolite Y, to improve gasoline octane and LPG yields.

In another embodiment of the invention, the ZSM-5 zeolite additive is prepared as a separate microsphere and contains phosphorus stabilized ZSM-5 zeolite, alumina, and kaolin bound together with phosphoric acid.

The ZSM-5 can be modified using phosphorus-containing compounds. Any phosphorus-containing compound having a covalent or ionic constituent capable of reacting with hydrogen ion may be employed such as, for example, phosphoric acid, phosphines and phosphites. Suitable phosphorus-containing compounds include derivatives of groups represented by $PX_3$, $RPX_2$, $R_2 PX$, $R_3 P$, $R_3 P=O$, $RPO_2$, $RP(O)(OX)_2$, $R_2 P(O)OX$, $RP(OX)_2$, $ROP(OX)_2$ and $(RO)_2 POP(OR)_2$ where R is an alkyl or phenyl radical and X is hydrogen, R or halide. These compounds include primary, $RPH_2$, secondary, $R_2 PH$, and tertiary, $R_3 P$, phosphines such as butyl phosphine; the tertiary phosphine oxides, $R_3 PO$, such as tributylphosphine oxide; the primary $RP(O)(OX)_2$ and secondary $R_2 P(O)OX$, phosphonic acids such as benzene phosphonic acid; the esters of the phosphonic acids such as diethyl phosphonate, $(RO)_2 P(O)H$, dialkyl alkyl phosphonates, $(RO)_2 P(O)R$, and alkyl dialkylphosphinates, $(RO)P(O)R_2$; phosphinous acids, $R_2 POX$, such as diethylphosphinous acid, primary $(RO)P(OX)_2$, secondary, $(RO)_2 POX$ and tertiary, $(RO)_3 P$, phosphites; and esters thereof such as the monopropyl ester, alkyl dialkylphosphinites, $(RO)PR_2$ and dialkyl alkylphosphonite, $(RO)_2 PR$ esters. Examples of phosphite esters include trimethylphosphite, triethylphosphite, diisopropylphosphite, butylphosphite; and pyrophospites such as tetraethylpyrophosphite. The alkyl groups in the mentioned compounds contain 1 to 4 carbon atoms.

Other suitable phosphorus-containing compounds include the phosphorus halides such as phosphorus trichloride, bromide and iodide, alkyl phosphorodichloridites, (RO)PCl.sub.2, dialkyl phosphorochloridites, $(RO)_2 PX$, dialkylphosphinochloridites, $R_2 PCl$, alkyl alkylphosphonochloridates, $(RO)(R)P(O)Cl$, and dialkyl phosphinochloridates, $R_2 P(O)Cl$.

Preferred phosphorus-containing compounds include: phosphoric acid, ammonium dihydrogen phosphate, diammonium hydrogen phosphate, or ammonium polyphosphate, trimethyl phosphite and phosphorus trichloride.

It is believed that the constituent of the phosphorus-containing compound capable of reacting with a hydrogen ion reacts with the hydrogen of the original zeolite. This would suggest that the phosphorus may be chemically bonded to the crystal structure of the zeolite since phosphorus-containing zeolites can be used for extended periods of time at high temperatures without loss of phosphorus. Further, it is not likely the phosphorus is present as a crystalline framework constituent, i.e., it has not been substituted for silicon or aluminum atoms, since the unit cell dimensions of the zeolite are unchanged on incorporation of the phosphorus atoms.

Incorporation of the phosphorus with the zeolite provides a composition having unique properties as a catalytic agent. The zeolites possess strong acid sites. On the other hand, the phosphorus-containing zeolite does not possess these strong acid sites. The phosphorus-containing zeolite possesses a greater number of acid sites than the parent zeolite but these sites appear to have a lesser acid strength than those found in the parent zeolite. It is believed that the apparent replacement of the strong acid sites with a greater number of relatively weak acid sites may be responsible for the unique catalytic properties of the phosphorus-containing zeolite.

Reaction of the zeolite with the phosphorus-containing compound is effected by contact. Where the phosphorus-containing compound is a liquid, said compound can be in solution in a solvent at the time contact with the zeolite is effected. Any solvent relatively inert with respect to the phosphorus-containing compound and the zeolite may be employed. Suitable solvents include aliphatic, aromatic or alcoholic liquids. Where the phosphorus-containing compound is trimethylphosphite or liquid phosphorus trichloride, a hydrocarbon solvent such as n-octane may be employed. The phosphorus-containing compound may be used without a solvent, i.e., may be used as a neat liquid. Where the phosphorus-containing compound is in the gaseous phase, such as where gaseous phosphorus trichloride is employed, the phosphorus-containing compound can be used by itself or can be used in admixture with a gaseous diluent relatively inert to the phosphorus-containing compound and the zeolite such as air or nitrogen.

Preferably, prior to reacting the zeolite with the phosphorus-containing compound, the zeolite is dried. Drying can be effected in the presence of air. Elevated temperatures may be employed. However, the temperature should not be such, as mentioned hereinafter, that the crystal structure of the zeolite is destroyed.

Heating of the phosphorus-containing catalyst subsequent to preparation and prior to use is also preferred. The heating can be carried out in the presence of oxygen, for example air. Heating can be at a temperature of about 150° C. However, higher temperatures, i.e., up to about 500° C. are preferred. Heating can be carried out for 1-24 hours. It has been found that heating increases the catalyst efficiency of the phosphorus-containing zeolite probably due to an increase in the number of acid sites rather than an increase in the strength of the existing acid sites. Increasing the heating temperature increases the catalyst efficiency. However, while heating temperatures above about 500° C. can be employed, they are not necessary. At temperatures of about 1000° C., the crystal structure of the zeolite is destroyed.

The amount of phosphorus incorporated with the crystal structure of the phosphorus-containing zeolite should be at least 0.1% by weight. With this amount of phosphorus, replacement of a sufficient proportion of the strong acid sites of the zeolite with an increased number of weaker acid sites is effected. In order to accomplish this it is preferred that the amount of phosphorus in the phosphorus-containing zeolite be at least about 0.5% by weight. The amount of phosphorus can be as high as 10% by weight, although with these higher amounts a decline in catalytic activity can occur.

In addition, the large-pore molecular sieve catalyst component described above may also include phosphorus or a phosphorus compound for any of the functions generally attributed thereto.

As discussed above, ZSM-5 selectively cracks gasoline range aliphatic molecules to form additional light olefins at the penalty of gasoline yield. Using phosphorus-containing ZSM-5 as FCC additives instead can reduce the gasoline yield loss and still effectively enhance light olefin yields. The yields of 2-methyl-butenes and n-butenes also increase when using phosphorus-containing ZSM-5 as the additive, due to its more moderate acid strength. Untreated ZSM-5, on the other hand, will further crack these $C_5$ and $C_4$ olefins due to its high acid strength. Therefore, when phosphorus-containing ZSM-5 zeolites are used as additives to cracking catalysts, the yields of 2-methyl-butenes, n-butenes, and gasoline are improved over using the corresponding untreated ZSM-5 as an additive.

In another embodiment of the invention, the ZSM-5 zeolite is blended with the Y zeolite wherein the ZSM-5 zeolite additive is prepared according to U.S. Pat. No. 7,375,048. According to the '048 patent, a high solids kaolin slurry is mixed with a slurry containing ZSM-5, a high surface area alumina (pseudoboehmite type) and a low surface area alumina or similar high density, non-reactive inorganic material. The mixed slurry is pumped to a static mixture adjacent to the atomizer of a spray dryer. Phosphoric acid is then injected into the dispersed high solids mixed kaolin slurry and the acid-injected slurry is atomized into droplets in a spray dryer. The process provides microspheres which have good kaolin interparticle binding and excellent physical and chemical properties. Moreover, the microspheres can contain at least 30 wt. % ZSM-5 and due to the addition of the unreactive alumina or other high density, unreactive inorganic material, have high attrition resistance.

For the present invention, beta zeolite is added to the Y zeolite and ZSM-5 zeolite blend. Beta zeolite is a crystalline zeolite whose composition and X-ray powder diffraction analysis are disclosed in U.S. Pat. Re No. 28,341, herein incorporated by reference in its entirety. This zeolite is a large pore zeolite having a pore size above 7.0 angstroms and a Constraint Index below 2. Beta zeolite is prepared, in general, as an aluminosilicate zeolite having a silica-to-alumina molar ratio ($SiO_2/Al_2O_3$) of at least 10. It may also be prepared in yet higher silica-to-alumina mole ratios, e.g., 500:1 or more, and although such materials may have little or no zeolitic properties, it is to be understood that, in the present invention, the term "Beta zeolite" is meant to encompass such materials.

Beta zeolite is usually synthesized from a reaction mixture containing a templating agent. The use of templating agents for synthesizing beta zeolite is well known in the art. For example, U.S. Pat. No. 3,308,069 and Re No. 28,341 describe using tetraethylammonium hydroxide and U.S. Pat. No. 5,139,759, which is hereby incorporated herein by reference in its entirety, describes using the tetraethylammonium ion derived from the corresponding tetraethylammonium halide. Another standard method of preparing beta zeolite is described in the book titled Verified Synthesis of Zeolitic Materials, by H. Robson (editor) and K. P. Lillerud (XRD Patterns), second revised edition, ISBN 0-444-50703-5, Elsevier, 2001. It is believed that the choice of a particular templating agent is not critical to the success of the process disclosed herein. In one embodiment, the beta zeolite is calcined in air at a temperature of from 500 to 700° C. for a time sufficient to remove to remove the templating agent from the beta zeolite. Calcination to remove the templating agent can be done before or after the beta zeolite is combined with the support and/or the hydrogenation component. Although it is believed that the templating agent could be removed at calcination temperatures above 700° C. Very high calcination temperatures could significantly decrease the $SF_6$ adsorption capacity of beta zeolite. For this reason it is believed that calcination temperatures above 750° C. for removing the templating agent should be avoided when preparing the beta zeolite for use in the process disclosed herein. It is critical to the process disclosed herein that the $SF_6$ adsorption capacity of the beta zeolite is at least 28 wt-%.

However, template free synthesis of Beta zeolite has been demonstrated in U.S. Published Application No. US2010/0322847, BASF. In another embodiment of the invention, the Beta zeolite additive for the present invention is prepared similar to the ZSM-5 additive and according to U.S. Pat. No. 7,375,048.

In still another embodiment of the invention, the form of the Beta zeolite is as H-Beta with a silica/alumina ratio greater than 10, further exemplified by silica/alumina ratios greater than 35. The silica/alumina ratio of the H-Beta zeolite can also be greater than 100.

Stabilization of the Beta zeolite with phosphorus in the present invention can be achieved by direct reaction of Beta zeolite with phosphoric acid or by incorporating the phosphoric acid into the additive via direct injection during the spray drying process. Ammonium hydrogen phosphates, or polyphosphate as described earlier for the ZSM-5 additive can also be used.

In another embodiment of the invention, the phosphorus level on the Beta zeolite is between 1 and 7% $P_2O_5$.

In another embodiment of the invention, the phosphorus level on the Beta zeolite is between 3 and 5% $P_2O_5$. Adding the phosphoric acid via inline injection during spray drying of the Beta additive required a preferred total phosphorus level of between 10 and 15% $P_2O_5$ with a more preferred level of 12-13% $P_2O_5$.

In another embodiment of the invention, the Y zeolite is Naphthamax® (rare earth exchanged Y zeolite crystallized in situ in a porous kaolin matrix) and is blended with the additive containing ZSM-5 zeolite, described above. A separate catalyst particle additive containing Beta zeolite, described above, is added to the catalyst blend.

Example 1

Blends of the Beta additive with low rare earth exchanged Naphthamax® and ZSM-5 additive after steam deactivation (15-24 hours at 1500° F. and 100% steam) have been evaluated on the ACE™ using a paraffinic feedstock supplied by Reliance Industries. Beta zeolite has a high propensity to make olefins due to its low intrinsic hydride transfer capability. This can be observed in the high levels of isobutylene to isobutane in cracking reactions. Blend ratios for maximum propylene yield therefore are based on more Beta additive than Naphthamax® and more Naphthamax® than ZSM-5 additive. Such a formulation would be 50-60% Beta additive, 25-30% 1% REO Naphthamax® and 15-20% ZSM-5 additive. Such a formulation gives propylene yields 1.5-2.5% higher than with the current state of the art Petrochemical FCC catalyst.

Single point catalyst/oil cracks were carried out on the ACE of eight blends: four using 50% Beta catalyst and four using 60% Beta catalyst. The amount of ZSM-5 and Naphthamax® were then varied to make up the balance of the blend. Table 1 gives the blend ratios and the conversions and propylene yields at the C/O of 10.26.

TABLE 1

| Catalyst Blend | % Naphthamax | % ZSM-5 Additive | % Beta Catalyst | C/O | Conversion Wt. % | Propylene Wt % |
|---|---|---|---|---|---|---|
| A | 40 | 10 | 50 | 10.26 | 74.2 | 15.5 |
| B | 35 | 15 | 50 | 10.26 | 73 | 15.5 |
| C | 30 | 20 | 50 | 10.26 | 74.1 | 16.3 |
| D | 25 | 25 | 50 | 10.26 | 71.2 | 16.2 |
| E | 30 | 10 | 60 | 10.26 | 72.8 | 15.8 |
| F | 25 | 15 | 60 | 10.26 | 71.2 | 16.2 |
| G | 20 | 20 | 60 | 10.26 | 69.2 | 15.3 |
| H | 15 | 25 | 60 | 10.26 | 66.1 | 15.2 |

It can be seen from Table 1 that blends C, D, and F have the highest yields of propylene and acceptable activity.

Example 2

A catalyst composition comprised of a blend of 60% Beta additive, 25% 1% REO Naphthamax and 15% ZSM-5 additive was prepared. The propylene yield of this catalyst composition is compared with a prior art Petrochemical FCC catalyst containing 23.5% ZSM-5 additive and 76.5% 1% REO Naphthamax. ACE testing using Reliance feed gave an increase in propylene yield of over 2%.

The invention claimed is:

1. A hydrocarbon conversion catalyst blend comprising:
   (a) a Y zeolite in an amount of 5 to 50 wt. % of said catalyst blend;
   (b) a ZSM-5 zeolite in an amount of 5 to 40 wt. % of said catalyst blend; and
   (c) a Beta zeolite in an amount of 35 to 70 wt. % of said catalyst blend, wherein each of said ZSM-5 zeolite, said Beta zeolite, and said Y zeolite is a separate microsphere.

2. The catalyst blend of claim 1, wherein the Y zeolite is a large-pore zeolite comprising Y zeolite crystallized as a layer on the surface of a porous alumina-containing matrix, said zeolite-layered matrix arranged in a configuration to provide macropores in which the zeolite layer is provided on the walls of the macropores.

3. The catalyst blend of claim 1, wherein the Y zeolite contains up to 12% of a rare earth element ion exchanged onto the Y zeolite.

4. The catalyst blend of claim 1 wherein the ZSM-5 additive contains zeolite comprises phosphorus stabilized ZSM-5 zeolite, alumina, and kaolin bound together with phosphorus-containing compound.

5. The catalyst blend of claim 1 wherein the Beta zeolite is a H-Beta with a silica/alumina ratio greater than 10.

6. The catalyst blend of claim 5 wherein the silica/alumina ratio of the Beta zeolite is greater than 100.

7. The catalyst blend of claim 1 wherein the Beta zeolite is modified with a phosphorus-containing compound.

8. The catalyst blend of claim 7 wherein the Beta zeolite has a phosphorus level between 1-7% $P_2O_5$.

9. The catalyst blend of claim 8 wherein the phosphorus level is between 3-5% $P_2O_5$.

10. The catalyst blend of claim 1 wherein the catalyst comprises 25-30 wt. % of said Y zeolite, 15-20 wt. % of said ZSM-5 zeolite, and 50-60 wt. % of said Beta zeolite.

11. A hydrocarbon conversion catalyst blend comprising:
    (a) a Y zeolite, wherein the Y zeolite is a large-pore zeolite comprising Y zeolite crystallized as a layer on the surface of a porous alumina-containing matrix, said zeolite-layered matrix arranged in a configuration to provide macropores in which the zeolite layer is provided on the walls of the macropores;
    (b) a ZSM-5 zeolite; and
    (c) a Beta zeolite,
    wherein said blend contains by wt. % more said Beta zeolite than said Y zeolite, and more said Y zeolite than said ZSM-5 zeolite, and each of said ZSM-5 zeolite, said Beta zeolite, and said Y zeolite is a separate microsphere.

12. The catalyst of claim 11 wherein the catalyst blend comprises 5-50 wt. % of said Y zeolite, 5-40 wt. % ZSM-5 zeolite, and 35-70 wt. % of said Beta zeolite.

13. The catalyst of claim 11 wherein the catalyst blend comprises 25-30 wt. % of said Y zeolite, 15-20 wt. % of said ZSM-5 zeolite, and 50-60 wt. % of said Beta zeolite.

14. The catalyst of claim 11 wherein the ZSM-5 zeolite is a phosphorus stabilized ZSM-5 zeolite, alumina, and kaolin bound together with a phosphorus-containing compound.

15. The catalyst of claim 14, wherein the Y zeolite contains 1% or less of a rare earth element ion exchanged onto the Y zeolite.

16. The catalyst of claim 14 wherein the Beta zeolite is a H-Beta with a silica/alumina ratio greater than 100.

17. The catalyst of claim 14 wherein the Beta zeolite is modified with a phosphorous-containing compound.

18. A process for the improved production of propylene comprising cracking a hydrocarbon feedstock under fluid catalytic cracking conditions with the catalyst of claim 1.

19. A process for the improved production of propylene comprising cracking a hydrocarbon feedstock under fluid catalytic cracking conditions with the catalyst of claim 15.

* * * * *